| United States Patent [19] | [11] Patent Number: 4,741,857 |
| Horwitz et al. | [45] Date of Patent: May 3, 1988 |

[54] METHOD OF PURIFYING NEUTRAL ORGANOPHOSPHORUS EXTRACTANTS

[75] Inventors: E. Philip Horwitz; Ralph C. Gatrone, both of Naperville, Ill.; Renato Chiarizia, Rome, Italy

[73] Assignee: The United States of America as represented by the United States Department of Energy, Washington, D.C.

[21] Appl. No.: 915,844

[22] Filed: Oct. 6, 1986

[51] Int. Cl.$^4$ .............. C09K 3/00; C07F 9/08; C07F 9/09; C07F 9/53

[52] U.S. Cl. .................. 252/184; 252/364; 252/631; 558/150

[58] Field of Search ............. 558/150; 252/184, 364; 210/682, 685, 686

[56] References Cited

U.S. PATENT DOCUMENTS

| 2,615,924 | 10/1952 | Reents | 210/686 X |
| 2,682,468 | 6/1954 | Frampton | 210/685 X |
| 3,708,508 | 1/1973 | Schulz | 252/364 |
| 3,793,408 | 2/1974 | Schulz | 558/150 |
| 3,993,728 | 11/1976 | Schulz | 423/9 |
| 4,051,203 | 9/1977 | Schulz | 558/150 |
| 4,276,235 | 6/1981 | McIsaac et al. | 558/150 |
| 4,540,493 | 9/1985 | Dickerson et al. | 210/685 X |
| 4,548,790 | 10/1985 | Horwitz et al. | 423/9 |
| 4,574,072 | 3/1986 | Horwitz et al. | 423/9 |

FOREIGN PATENT DOCUMENTS

33654  3/1977  Japan .................. 558/150

OTHER PUBLICATIONS

*Solvent Extraction and Ion Exchange*, 4(4), pp. 677-723 (1986), Renato Chiarizia and E. Philip Horwitz, "Hydrolytic and Radiolytic Degradation of Octyl(Phenyl)-N,N-Diisobutylcarbamoylmethylphosphine Oxide and Related Compounds".

*Primary Examiner*—Matthew A. Thexton
*Attorney, Agent, or Firm*—Thomas Anderson; James W. Weinberger; Judson R. Hightower

[57] ABSTRACT

A method for removing acidic contaminants from neutral mono and bifunctional organophosphorous extractants by contacting the extractant with a macroporous cation exchange resin in the H$^+$ state followed by contact with a macroporous anion exchange resin in the OH$^-$ state, whereupon the resins take up the acidic contaminants from the extractant, purifying the extractant and improving its extraction capability.

15 Claims, No Drawings

METHOD OF PURIFYING NEUTRAL ORGANOPHOSPHORUS EXTRACTANTS

CONTRACTUAL ORIGIN OF THE INVENTION

The U.S. Government has rights in this invention pursuant to Contract No. W-31-109-ENG-38 between the U.S. Department of Energy and Argonne National Laboratory.

BACKGROUND OF THE INVENTION

This invention relates to a method for removing acidic contaminants from organic extractants. More specifically, this invention relates to a method of removing acidic contaminants resulting from the preparation and from the radiolytic and hydrolytic degradation of neutral mono- and bifunctional organophosphorous compounds.

The recovery of multivalent lanthanide and actinide values from nitric acid nuclear fuel waste reprocessing solutions containing these values in combination with other metal and fission product values using the the alkyl(phenyl)-N,N-dialkylcarbamoylmethylphosphine oxides, hereinafter refered to as CMPO, is described in U.S. Pat. No. 4,548,790, dated Oct. 22, 1985. The combination of the CMPO extractants with a phase modifier such as tri-n-butylphosphate (hereinafter referred to as TBP) in a normal paraffin hydrocarbon (NPH) diluent is described in U.S. Pat. No. 4,574,072, dated Mar. 4, 1986. Both patents are assigned to the common assignee and are incorporated herein by reference.

The neutral organophosphorous compounds used for the reprocessing of irradiated nuclear reactor fuels, including monofunctional compounds such as TBP and bifunctional compounds such as the CMPO's, described above, and similar compounds such as dihexyl N,N-diethyl-carbamoylmethylenephosphonate (DHDECMP) are subject to a gradual, but continous hydrolytic and radiolytic degradation process which produce acidic compounds. These acidic compounds act as extractants, destroying the effectiveness of the extractants by preventing the effective stripping of certain radioactive values from the extractant phase. This problem is described in detail in *Solvent Extraction and Ion Exchange* 4(4), 677–723 (1986).

Furthermore, the preparation of these extractants produces soluble organic acidic compounds which also act as extractants. As explained above, the presence of these acidic extractants prevent stripping from taking place, greatly reducing the efficiency of the extractants and eventually reducing the ability to effect separation of the various values. This, in turn, results in the transuranium elements (TRU) either being recycled via the organic phase back into the extraction stages or the generation of a new transuranium element waste in the solvent clean-up reagent. The presence of TRU's in recycled organic solvent significantly reduce the decontamination factor than can be achieved using these extractants.

Several methods have been described for the purification of various neutral organophosphorous extractants. For example, U.S. Pat. No. 3,708,508 describes the purification of tri-n-butylphosphate (TBP) of chemical and radiolytic degradation products and fission products by passing the TBP through a strong base macroreticular anion exchange resin which absorbs many of the degradation products and metal values while recovering the purified TBP as the eluent.

Another method for purifying bidentate organophosphorous compounds of an unknown acidic contaminents is provided by U.S. Pat. No. 4,051,203. As described therein, the organophosphorous compounds, such as DHDECMP is diluted with a water-immiscible organic solvent such as $CCl_4$, to form an extractant. The extractant is then contacted with ethylene glycol, whereby the impurities are taken up by the ethylene glycol which is then separated from the purified extractant.

However, none of these processes are completely satifactory for purifying the neutral organophosphorous extractants and furthermore, none of the processes will purify a mixture of a bifunctional extractant such as CMPO and a monofunctional extractant such as TBP.

SUMMARY OF THE INVENTION

A method has been developed for which will remove the acidic contaminants found in commercial grade neutral organophosphorous extractants and also the acidic contaminants resulting from the hydrolytic and radiolytic degradation of irradiated organophosphorous extractants which have been used for the reprocessing of nuclear reactor fuel. By the method of this invention, the neutral organic extractant containing acidic contaminants, which may be in the salt or the acid form, is contacted with a macroporous cation exchange resin in the $H^+$ state to form a first mixture, maintaining the contact for a period of time and at a temperature sufficient to convert the salt form of the acidic contaminants to the acid form, adding a macroporous anion exchange resin in the $OH^-$ state to the first mixture to form a second mixture, maintaining the contact for a period of time and at a temperature sufficient for the anion resin to take up the acid form of the acidic contaminants from the mixture, and separating the ion exchange resins from the mixture, whereby the acidic contaminants remain with the ion exchange resins, thereby removing the acidic contaminants from the organophosphorous extractant.

It is therefore one object of the invention to provide a method for removing acidic contaminants from commercial grade neutral organophosphorous extractants. It is another object of the invention to provide a method for removing acidic contaminants resulting from radiolytic and hydrolytic degradation from neutral organophosphorous extractants. It is still another object of the invention to provide a method for removing acidic contaminants from commercial grade CMPO. It is yet another object of the invention to provide a method for removing acidic radiolytic and hydrolytic degradation products from CMPO which has been used as an extractant to reprocess irradiated nuclear reactor fuel. It is still a further object of the invention to remove acidic contaminants from mixtures of CMPO and TBP. Finally, it is the object of the invention to remove acidic contaminants from mixtures of CMPO and TBP which have been used to reprocess irradiated nuclear reactor fuel.

DETAILED DESCRIPTION OF THE PREFERRED EMBODIMENT

These and other objects of the invention for the removal of acidic contaminants, which may be in the salt or acid form, from neutral bifunctional organophosphorous extractants consists of dissolving octyl (phenyl)N,N-diisobutylcarbamoylmethyl phosphine oxide (hereinafter O$\phi$D(iB)CMPO) in normal heptane as a diluent to form a solution containing about 0.75M O$\phi$D(iB)CMPO, adding a macroporous strong acid cation exchange resin in the H$^+$ state to the solution, at a ratio of about 50 grams resin/liter solution, to form a first mixture, agitating the first mixture for about 30 minutes at a temperature of about 50° C., to convert the salt form of the acidic contaminant to the acid form, adding a macroporous strong base anion exchange resin in the OH$^-$ state to the first mixture, at a ratio of 50 grams resin/liter solution, to form a second mixture, agitating the second mixture for about 30 minutes at a temperature of about 50° C., whereby the anion resin takes up the acid form of the acidic contaminant, and filtering the mixture to separate the ion exchange resins from the extractant solution, thereby removing the acidic contaminants from the O$\phi$D(iB)CMPO.

The method of the invention is particularly useful for the removal of acidic contaminants and acidic radiolytic and hydrolytic degradation products from mixtures of TBP and the bifunctional organophosphorous extractants such as the CMPO's and most specifically when TBP is combined with O$\phi$D(iB)CMPO as in the modified Purex process solvent.

The organic extractant diluent may be any suitable water-immicible organic compound in which the organophosphorous extractant is soluble and which has a boiling point above the temperature at which the method of the invention is being run. Generally, a boiling point of at least 50° C. will be sufficient. Examples of suitable diluent are the normal paraffin hydrocarbons (NPH) such as heptane or hexane or the chlorinated hydrocarbons such as carbon tetrachloride or tetrachloroethylene. When the CMPO's are being purified, TBP is a suitable diluent.

The amount of diluent in the solution should be the minimum amount necessary for the extractant to mix well with the resins and generally may vary from about 0.25M extractant up to about 1.0M, although about 0.75M is preferred. TBP may be purified undiluted and may be used as a diluent for the CMPO extractants in place of the NPH or chlorinated hydrocarbons.

The ion exchange resin in the first mixture may be any macroporous strong acid cation exchange resin in the H$^+$ form, such as Dowex ® AG-MP50 or Amberlyst ® 15.

The ion exchange resin in the second mixture may be any macroporous strong base anion exchange resin in the OH$^-$ form such as, for example, Amberlyst ® A-26.

The quantity of ion exchange resin will depend upon the amount of acidic contaminents present in the extractant and must be an amount sufficient to convert the salt form of the acidic contaminants to the acid form and remove the acid form from the extractant. Generally, it has been found that about 50 grams of each resin per liter of diluted solution is sufficient to obtain satisfactory results.

The contact time between the resins and the extraction solution must be sufficient to convert and remove the acidic contaminants from the solution, as will be discussed hereinafter. Generally, it has been found that with vigorous contact, a time of at least 30 minutes has been sufficient to achieve satisfactory results. Contact should be sufficiently vigorous, such as by stirring or agitation, to ensure complete contact between the resins and the solution.

The process temperature must be sufficient to result in the removal of the acidic contaminants from the extractant. Generally a temperature of at least 50° C. have been found sufficient although the temperature may be higher. The temperature should not be above the boiling point of the diluent.

It is important that the resins be contacted with the extractant in the order given, i.e. the cation resin first, followed, after a sufficient period of time, by the anion resin. As will be shown by the following Examples, the cation ion resin alone achieves no purification, while the anion resin alone will reduce the acidic impurities to some extent, but is not nearly as effective as the combination of resins. While we do not wish to be bound by the following explanation, it is believed that the mechanism of acidic contamination removal takes place as follows: The acidic impurities are present in the extractant in both a salt and an acid form. The cation resin reacts with the salt form and converts it to the acid form, the cation resin then taking up the salt. The anion resin reacts with the acid form to complex the acid impurity and remove it, forming water. Other acid impurities in the solution react to produce new salt forms. The new salt forms react with the cation resin to be converted to the acid form which is then complexed by the anion resin and removed from the extractant.

After completion of the addition of the anion exchange resin and agitation for the appropriate period of time, the resins may be separated from the solution by any suitable means, such as, for example, decantation or by filtration.

The purified extractant is now ready to be cycled back to the extraction process although in some circumstances it may be necessary to remove excess diluent from the extractant. Mixtures of CMPO and TBP can be recycled back to the extraction process without further processing.

The following examples are given to illustrate the process of the invention and are not to be taken as limiting the scope of the invention as defined by the appended claims.

EXAMPLE I

A 0.75 m solution of technical grade octyl(phenyl)-N,N-diisobutylcarbamoylmethylphosphine oxide (hereinafter CMPO) in heptane containing acidic components or their salts, was determined to have an elevated distribution coefficient ($D_{Am}$) for americium of 0.26 from 0.01M nitric acid. The solution was warmed in a water bath to 50° C. and 50 gm per liter of Dowex ® AG-MP50 cation exchange resin in the H$^+$ form was added to the solution. After stirring for 30 minutes, 50 gm per liter of Amberlsyt ® A-26 in the OH$^-$ form was added to the solution. Stirring was continued for an additional 30 minutes. The combined resins were removed by vacuum filtration using a coarse glass fritted funnel. The organic phase was consequently washed with 1:1 phase volumes of 5% Na$_2$CO$_3$(aq), 0.5M HNO$_3$(aq) and twice with water. After drying over anhydrous Na$_2$SO$_4$, the organic phase was filtered and concentrated at reduced pressure. The distribution coefficient, measured for a 0.25M extractant concentration in tetrachloroethylene, for americium at 0.01M nitric acid was found to be 0.019, a 13-fold improvement.

EXAMPLE II

In order to test the effect of temperature on the removal of acid contaminants from the CMPO extractent, a sample of CMPO was treated exactly as in Example I except that the temperature was maintained at 22° C. rather than at 50° C. The distribution coefficient of the treated CMPO for americium from 0.01M nitric acid was found to be 0.032.

EXAMPLE III

An impure sample of CMPO was treated at 50° C. as in Example I except that the prescribed amounts of each resin were simultaneously introduced into the solution which was then stirred for 1 hour. The distribution coefficient was found to be 0.093.

EXAMPLE IV

An impure sample of CMPO was treated at 50° C. as described in Example I with the exception that the order of resin introduction was reversed. The distribution coefficient for Am was found to be 0.068.

EXAMPLE V

In the same manner as before, an impure sample of CMPO was treated at 50° C. except that Amberlyst ® 15 cation exchange resin in the $H^+$ from was substituted for Dowex ® AG-MP50. The distribution coefficient for americium was determined to be 0.023.

EXAMPLE VI

An impure sample of CMPO in heptane was treated with the 50 g/L of Amberlyst ® A-26 for 60 min at 50° C. The distribution coefficient was found to be 0.089, indicating only slight improvement.

EXAMPLE VII

An impure sample of CMPO in heptane was treated with Dowex ® AG-MP50 cation exchange resin for 60 min. The distribution coefficient was found to be 0.33 indicating that no impurities were removed.

EXAMPLE VIII

A sample of tributylphosphate containing acidic components or their salts was warmed to 50° C. A cation exchange resin (Dowex ® AG-MP50) was added at 50 g/L. After stirring for 30 minutes, Amberlyst ® A-26 (an anion exchange resin, 50 g/L) was added and stirring was continued for 30 min., while maintaining the temperature at 50° C. The combined resins were removed by filtration and the purity was established by improved Pu stripping properties where 99.99% of the Pu was removed by a single contact with aqueous 1M HCl (1:1 phase ratio).

EXAMPLE IX

An impure sample of CMPO (0.25M) in heptane was contacted for 30 min. at room temperature with 1M hydrochloric acid (aq). After phase separation, the organic phase was contacted with 1M sodium hydroxide (aq) for 30 min. at room temperature. After phase separation, the organic phase was dried over anhydrous sodium sulfate, filtered and was concentrated at reduced pressure. A 0.25M solution in tetrachlorothylene provided a value for the distribution coefficient for americium of 0.35, indicative of no purification.

EXAMPLE X

A solution, 0.25M in CMPO and 1.0M in TBP in tetrachloroethylene, observed to be impure based upon a distribution ratio of Am in aqueous sulfanilic acid of 0.15, was treated with 50 qm per liter of Dowex ® AGMP 50 ®, 50° C., followed in 30 minutes by 50 gm per liter of Amberlyst A26 ® as per Example I. The distribution coefficient was remeasured in aqueous sulfanilic acid and found to be 0.0037.

As can be seen from the proceeding discussion and Examples, the method of the invention for the removal of acidic contaminants from neutral mono and bifunctional organophosphorous extractants and from mixtures of bifunctional organophosphorous extractants and tributylphosphate, and represents a significant improvement over prior art methods of removing acidic contaminants from these extractants.

The embodiments of this invention in which an exclusive property or privilege is claimed are defined as follows:

1. A method of removing acidic contaminants from neutral mono and/or bifunctional organophosphorous extractants comprising:
    contacting the extractant with a macroporous strong acid cation exchange resin in the $H^+$ state to form a first mixture,
    maintaining the contact for about 30 minutes at about 50° C.,
    contacting the first mixture with a macroporous strong base anion exchange resin in the $OH^-$ state to form a second mixture,
    maintaining the contact for about 30 minutes at about 50° C. whereby the resins take in the acidic contaminants, and
    separating the extractants from the resins containing the contaminated, thereby removing the contaminants from the extractant.

2. A method of removing acidic contaminants, present in a salt or acid form, from neutral mono and/or bifunctional organophosphorous extractants comprising:
    contacting the extractant with a macroporous strong acid cation exchange resin in the $H^+$ state to form a first mixture,
    maintaining said contact for a period time and at a temperature sufficient to convert the salt form of the acidic contaminant into the acid form,
    contacting the first mixture with a macroporous strong base anion exchange resin in the $OH^-$ state to form a second mixture,
    maintaining said contact for a period of time and at a temperature sufficient for the anion resin to take up the acid form of the contaminant from the mixture, and
    separating the extractant from the resins containing the contaminants, thereby removing the acidic contaminants from the extractant.

3. The method of claim 2 wherein the extractant is a bifunctional organophosphorous extractant and the extractant is present in a diluent to form a solution, the diluent being a water-immiscible organic compound in which the extractant is soluble and which has a boiling point above the temperature of the solution.

4. The method of claim 3 wherein the diluent has a boiling point above about 50° C. and is selected from the group consisting of the normal paraffin hydrocarbons, the chlorinated hydrocarbons and tri-n-butyl-phosphate.

5. The method of claim 4 wherein the diluent is selected from the group consisting of the normal paraffin hydrocarbons and the chlorinated hydrocarbons and the extractant is present in the diluent in a concentration of from about 0.25 to 1.0M.

6. The method of claim 5 wherein the solution is about 0.75M in extractant, the temperature is at least 50° C. and the resins are present in a ratio of at least 50 grams resin/liter of solution.

7. The method of claim 6 wherein the diluent is elected from the group consisting of heptane, hexane, carbon tetrachloride and tetrachloroethylene.

8. The method of claim 7 wherein the bifunctional extractant is octyl(phenyl)N,N-diisobutylcarbamoylmethylphosphine oxide, the diluent contains 0.75M of the extractant, and contact with each resin was maintained for about 30 minutes.

9. The method of claim 4 wherein the extractant is the monofunctional organophosphorous compound tri-n-butylphosphate.

10. The method of claim 9 wherein the extractant is present EN a diluent to form a solution, the diluent being selected from the group consisting of the normal paraffin hydrocarbons and the chlorinated hydrocarbons, the solution being from about 0.25 to 1.0M in extractant.

11. The method of claim 10 wherein the diluent is about 0.75M in extractant, the temperature is at least 50° C. and the resins are present in a ratio of at least 50 grams resin/liter of solution.

12. A method of removing acidic contaminants, present in a salt or acid form, from octyl(phenyl)N,N-diisobuty-carbonoylmethylphosphine oxide extractant comprising:

dissolving the extractant in a diluent selected from the group consisting of heptane, hexane, carbon tetrachloride and tetrachloroethylene to form a solution from 0.25 to 1.0M in extractant, adding a macroporous strong acid cation exchange resin in the H$^+$ state to the solution, at a ratio of about 50 grams resin/liter solution, to form a first mixture, agitating the first mixture for a period of time and at a temperature sufficient to convert the salt form of the acidic contaminants to the acid form, adding a macroporous strong base anion exchange resin in the OH$^-$ state to the solution at a ratio of about 50 grams resin/liter solution to form a second mixture, agitating the second mixture for a period of time and at a temperature sufficient for the resin to take up the acid form of the acidic contaminant, and filtering the second mixture to separate the ion exchange resins from the extractant solution thereby removing the acidic contaminants from the extractant.

13. The method of claim 12 wherein the solution contains 0.75M extractant.

14. The method of claim 13 wherein the solution also contains about 1.0M tri-n-butylphosphate.

15. The method of claim 14 wherein the first and second mixtures each are agitated for about 30 minutes at 50° C.

* * * * *